United States Patent [19]

Herzog

[11] Patent Number: 5,504,958
[45] Date of Patent: Apr. 9, 1996

[54] ELECTRIC TOOTHBRUSH

[75] Inventor: Karl Herzog, Frankfurt, Germany

[73] Assignee: Braun Aktiengesellschaft, Kronberg, Germany

[21] Appl. No.: 347,906

[22] Filed: Dec. 1, 1994

[30] Foreign Application Priority Data

Dec. 17, 1993 [DE] Germany .................. 43 43 103.8

[51] Int. Cl.$^6$ .................................................. A61C 17/34
[52] U.S. Cl. ................................................................. 15/22.1
[58] Field of Search .................................. 15/22.1, 22.2, 15/22.4; 433/216

[56] References Cited

U.S. PATENT DOCUMENTS

| | | | |
|---|---|---|---|
| 5,077,855 | 1/1992 | Ambasz | 15/22.1 |
| 5,259,083 | 11/1993 | Stansbury, Jr. | 15/22.1 |

FOREIGN PATENT DOCUMENTS

| | | | |
|---|---|---|---|
| 3931982A1 | 4/1991 | Germany | 15/22.1 |
| 2247297 | 2/1992 | United Kingdom | 15/22.1 |

*Primary Examiner*—Edward L. Roberts, Jr.
*Attorney, Agent, or Firm*—Fish & Richardson

[57] ABSTRACT

The invention is directed to an electric toothbrush including a brush unit (1) adapted to be push-fitted to a handle unit. The brush unit (1) accommodates a rotary camshaft (4) as well as a series of bristle holders (11, 12, 13, 14, 15, 16) provided with tufts (17) of bristles and disposed approximately transversely relative to the camshaft (4). The bristle holders (11, 12, 13, 14, 15, 16) are pivotally mounted on two mounting pins (8, 9) extending parallel to the camshaft (4), thus enabling the bristle holders (11, 12, 13, 14, 15, 16) to be moved in a motion about the mounting pin (8, 9) by the camshaft (4). The two mounting pins (8, 9) are arranged on either side of an imaginary first plane (18) aligned approximately parallel to the bristle tufts (17) and extending lengthwise through the camshaft (4), and each of the bristle holders (11, 12, 13, 14, 15, 16) includes an opening (19, 20) for receiving one of the two mounting pins (8, 9). By virtue of the off-center arrangement of the two mounting pins (8, 9), the bristle tufts (17) perform not only a wiping motion approximately parallel to the tooth surface but also an additional pushing motion transversely relative to the tooth surface.

10 Claims, 2 Drawing Sheets

ELECTRIC TOOTHBRUSH

This invention relates to an electric toothbrush with a brush unit in which a camshaft is rotatably received and which includes a series of bristle holders provided with tufts of bristles and disposed approximately transversely relative to the camshaft, the bristle holders being pivotally mounted on a mounting pin which extends approximately parallel to the camshaft, and being movable in a motion about the mounting pin by the camshaft.

An electric toothbrush of this type is known from U.S. Pat. No. 5,077,855. In this specification, a brush unit is attachable to a handle unit of the electric toothbrush. The brush unit receives in the longitudinal direction a crankshaft or camshaft adapted to be rotated by an electric motor housed in the handle unit. The brush unit further includes six bristle holders each carrying projecting tufts of bristles. The bristle holders are arranged approximately transversely to the crankshaft, and the bristle tufts protrude approximately transversely from the brush unit. The bristle holders are provided with an approximately central hole through which a mounting pin extends in parallel arrangement with the crankshaft. In this construction, the mounting pin is disposed in the central longitudinal plane between the crankshaft and the bristle tufts. The crankshaft is provided with six crank pins or cams, each turned 180 degrees from the other. When the crankshaft is caused to rotate, this has the effect of successive bristle holders with their bristle tufts executing oscillating rotary motions about the mounting pin in opposite directions. When a user positions the bristle tufts against the tooth surface to be cleaned at approximately right angles, the tips of the bristle tufts execute a reciprocating motion substantially parallel to the tooth surface. However, in many cases such a merely wiping motion of the bristle tufts is not sufficient, particularly when it is desired to remove plaque completely.

Accordingly, it is an object of the present invention to provide an electric toothbrush which ensures an improved removal of plaque.

According to the present invention, this object is accomplished in that in an electric toothbrush of the type initially referred to the mounting pin is disposed outside an imaginary first plane aligned approximately parallel to the bristle tufts and extending lengthwise through the camshaft.

In contrast to the prior art referred to in which the bristle holders are mounted on the mounting pin approximately centrally, the bristle holders of the present invention are mounted off-center. As a result, the tips of the bristle tufts perform a motion including, in addition to a parallel and thus wiping component, a component at right angles thereto which is thus a pushing component. This pushing component is at its maximum level in those bristle tufts that are spaced the farthest from the mounting pin on which the bristle holder is mounted. When a user positions the bristle tufts against the tooth surface to be cleaned at approximately right angles thereto, the additional component of pushing motion of the bristle tufts produces a cleaning action on the teeth substantially higher than would be accomplished with a merely wiping component. The component of pushing motion ensures efficient loosening and removal also of stubborn contaminants adhering to the tooth surfaces, such as plaque, or interproximal deposits. The cleaning action of the toothbrush of the present invention is thus substantially improved by the pushing component of the bristle tuft movements.

In an advantageous embodiment of the present invention, two mounting pins are provided, one on either side of the imaginary first plane, and each of the bristle holders includes an opening for receiving a mounting pin. In this manner, one-sided movements of the bristle holders are avoided which would be produced by the off-center arrangement of a single mounting pin. Overall, the movements of the bristle holders are balanced out, enabling a user to manipulate the electric toothbrush in a simple and pleasant manner. Particularly suitably, the bristle holders are mounted on the two mounting pins alternately.

In a further advantageous embodiment of the present invention, the mounting pins are arranged in an imaginary second plane aligned approximately transversely relative to the bristle tufts and extending approximately parallel to the camshaft. Accordingly, the mounting pins, in addition to being arranged off-center, are also arranged in the imaginary second plane on either side of the camshaft. As a result, the component of the bristle tuft motions extending at approximately right angles to the tooth surface, being thus a pushing component, is particularly large. This improves the cleaning action of the toothbrush of the present invention still further.

In still another advantageous embodiment of the present invention, the two mounting pins are approximately parallel to each other, and the distances of the two mounting pins to the imaginary first plane are approximately equal. Thus, the mounting pins are approximately symmetrically arranged. It is thereby achieved that the movements in opposite directions of two successive bristle holders correspond to each other. Accordingly, the off-center arrangement of the mounting pins and the resultant pushing motion of the bristle holders does not result in a one-sided cleaning function, considering the entirety of all bristle holders. The improved cleaning action of the toothbrush of the present invention is thus further enhanced.

In an advantageous further feature of the present invention, each of the bristle holders has a recess in the area of the mounting pin on which it is not mounted, with the recess being configured such as to enable the bristle holder to perform the motion imparted to it by the camshaft, without making contact with this particular mounting pin. Accordingly, each of the bristle holders includes an opening for receiving one of the two mounting pins as well as a recess in the area of the other mounting pin. Each bristle holder is thus pivotal by the camshaft about its associated mounting pin, without being prevented from so moving by the other mounting pin.

In another advantageous feature of the present invention, each of the bristle holders includes an elongate hole for receiving the camshaft, with the longitudinal axis of the elongate hole intersecting approximately the geometric axis of the associated mounting pin. The effect accomplished by means of the elongate hole is that each bristle holder is accurately guided by the cams of the camshaft, thereby executing the intended motion. No further components are thus required to accomplish the enhanced cleaning effect of the toothbrush of the present invention.

In another advantageous embodiment of the present invention, the bristle holders are of identical configuration, irrespective of their mounting on one of the two mounting pins. The attendant advantages particularly as regards the manufacturing cost of the bristle holders are obvious.

In a further advantageous embodiment of the present invention, the camshaft is adapted to perform an oscillating rotary motion. This is suitable particularly when it is desired to utilize a handle unit in which the electric motor executes such an oscillating rotary motion.

Particularly conveniently, the bristle holders are provided with different tufts of bristles. This is conducive to enhancing the cleaning action still further.

Further features, advantages and application possibilities of the present invention will become apparent from the subsequent description of embodiments illustrated in more detail in the accompanying drawings. It will be understood that any feature set out and/or illustrated in the drawings, whether taken alone or in any desired combination, constitutes the subject-matter of the present invention, irrespective of their summarization in the claims and/or their back-references.

In the embodiment described, an electric toothbrush is comprised of a handle unit and a brush unit. Received in the handle unit is an electric motor capable of imparting continuous rotation to a drive shaft projecting from the handle unit. The brush unit is push-fitted to the handle unit so that the drive shaft of the handle unit extends into the brush unit.

In FIGS. 1 to 4, there is shown the free end of such a brush unit 1, including an approximately cylindrical or conical neck portion 2 and an adjoining cup-shaped mouthpiece 3.

Figure 1:
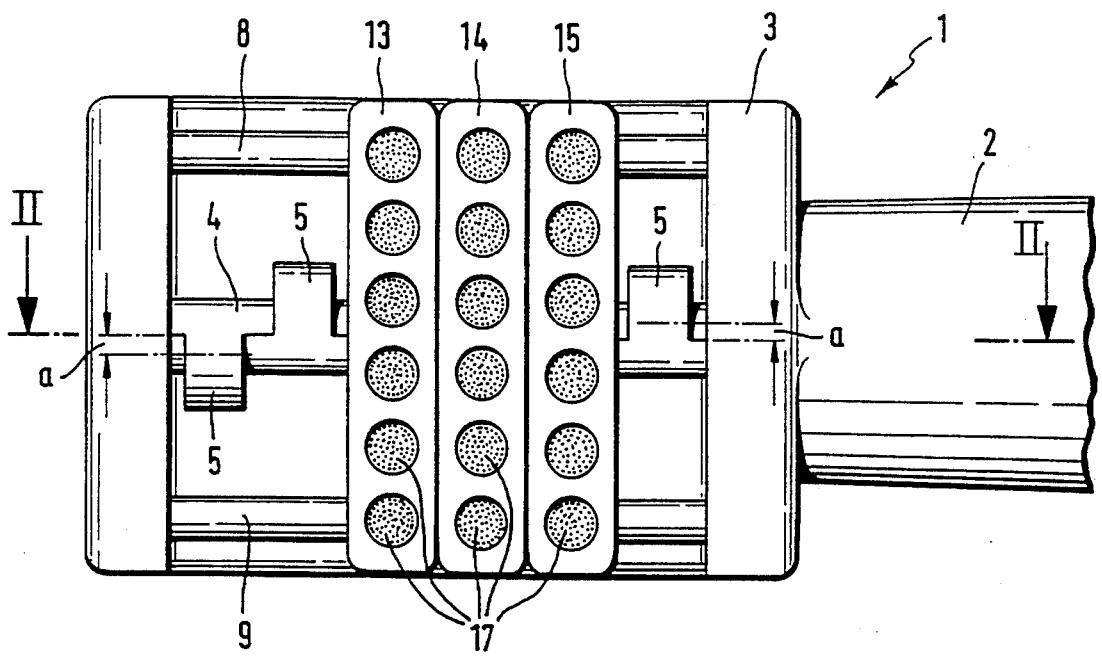
FIG. 1 is a schematic view of a brush unit of an electric toothbrush constructed in accordance with the present invention, as seen looking from the direction I in FIG. 2.
Figure 2:
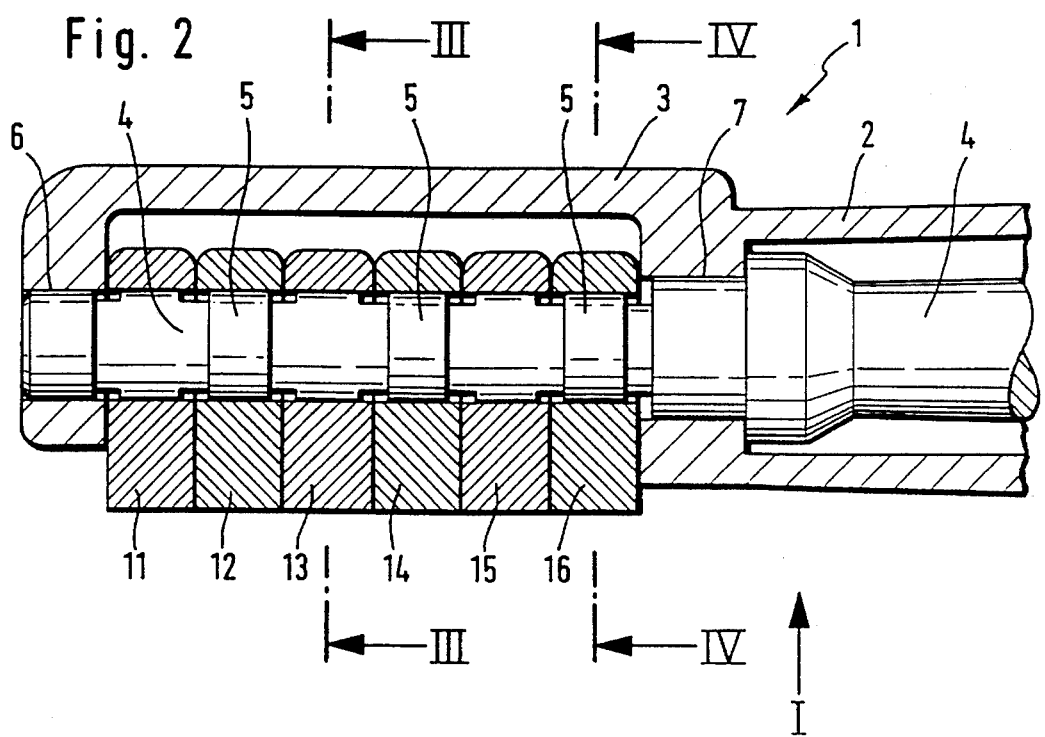
FIG. 2 is a schematic sectional view of the brush unit of FIG. 1, taken along the line II—II of FIG. 1.
Figure 3:
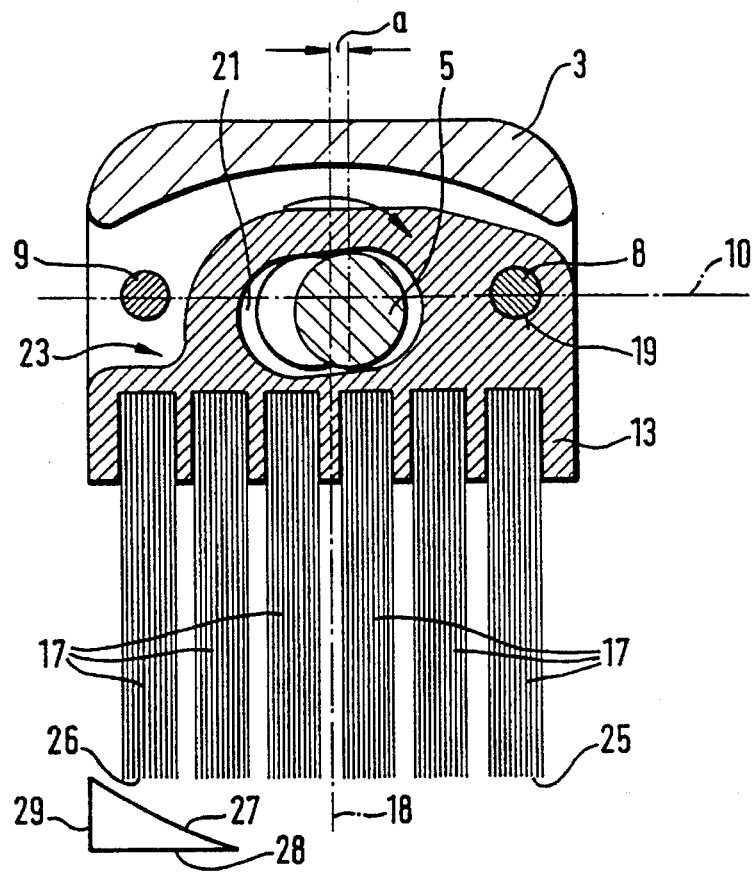
FIG. 3 and FIG. 4 are schematic sectional views of the brush unit of FIG. 1, taken along the lines III—III and, respectively, IV—IV of FIG. 2.
Figure 4:
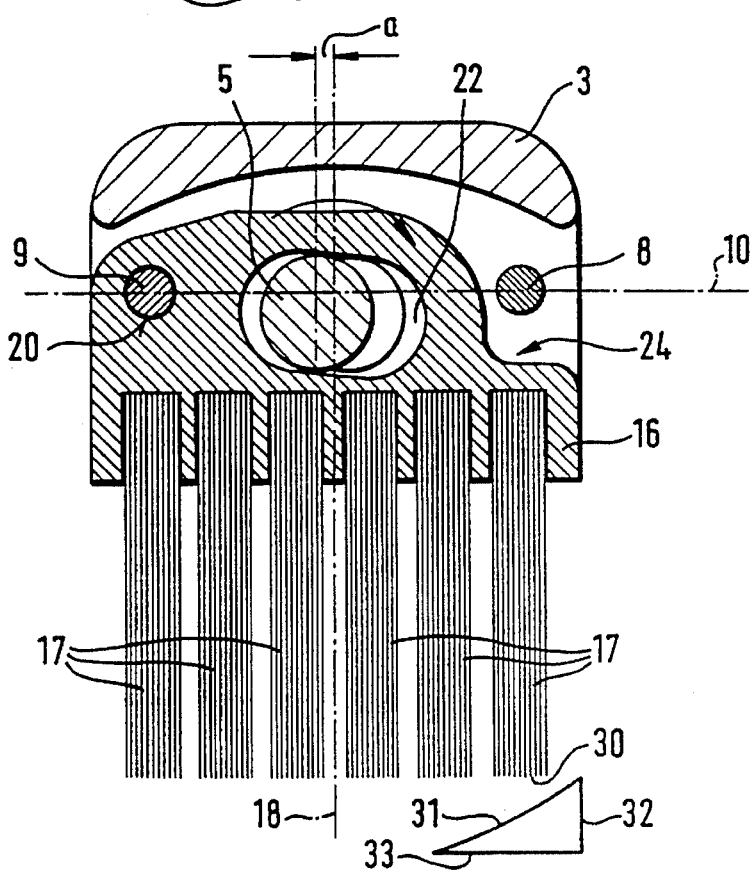

The neck portion 2 accommodates a camshaft 4 which is non-rotatably coupled to the drive shaft of the handle unit extending into the brush unit 1, its free end projecting into the mouthpiece 3. In the area of the mouthpiece 3, the camshaft 4 is provided with six cams 5 of circular cross-section arranged lengthwise in succession, of which two adjacent cams 5 each are circumferentially spaced apart by 180 degrees. The eccentricity of the cams 5 is illustrated in FIGS. 1, 3 and 4 by means of the distance a. The 180-degree offset orientation of the cams 5 becomes apparent particularly from FIG. 1.

The camshaft 4 is rotatably mounted in bearings 6, 7 provided in the end walls of the mouthpiece 3. This becomes particularly clear from FIG. 2. When the shaft driven by the electric motor is rotated, the camshaft 4 performs equally a rotary motion because it is rotationally fixed relative to the drive shaft.

Parallel to the camshaft 4, two mounting pins 8, 9 are provided, their respective free ends being carried in the end walls of the mouthpiece 3. The mounting pins 8, 9 are equidistantly spaced from the camshaft 4. As illustrated particularly in FIGS. 3 and 4, the two mounting pins 8, 9 are arranged on either side of the camshaft 4 in a common imaginary plane 10.

Mounted in an inner cavity of the mouthpiece 3 are six bristle holders 11, 12, 13, 14, 15, 16 of identical configuration. This becomes apparent particularly from FIGS. 3 and 4.

As appears from FIGS. 1 to 4, the bristle holders 11, 12, 13, 14, 15, 16 are configured in the form of flat, planar components of little thickness. They are arranged transversely relative to the camshaft 4, covering the width of the inner cavity of the mouthpiece 3. Each of the bristle holders 11, 12, 13, 14, 15, 16 is provided with a plurality of tufts 17 of bristles arranged approximately parallel to an imaginary plane 18 extending lengthwise through the camshaft 4 and approximately transversely relative to the plane 10 formed by the mounting pins 8, 9. The bristle tufts 17 protrude from the inner cavity of the mouthpiece 3, thereby enabling a user to position them against the tooth surface to be cleaned at approximately right angles thereto.

According to FIGS. 3 and 4, each of the bristle holders 11, 12, 13, 14, 15, 16 includes an opening 19, 20 in which one of the two mounting pins 8, 9 is received. The bristle holders 11, 12, 13, 14, 15, 16 are alternately associated with the two mounting pins 8, 9. As a result, the bristle holders 11, 13, 15 are mounted on the mounting pin 8, and the bristle holders 12, 14, 16 on the mounting pin 9.

Each of the bristle holders 11, 12, 13, 14, 15, 16 includes about centrally an elongate hole 21, 22 whose longitudinal axis intersects the geometric axis of the associated mounting pin 8, 9. The elongate hole 21, 22 is configured such as to receive therein one of the cams 5 of the camshaft 4. This becomes particularly clear from FIGS. 3 and 4. Further, the length of the cams 5 and the thickness of the bristle holders 11, 12, 13, 14, 15, 16 are conformed to each other such that each of the bristle holders 11, 12, 13, 14, 15, 16 registers exactly with one of the cams 5. This appears particularly from FIG. 2.

In the area of the mounting pin 8, 9 on which one of the bristle holders 11, 12, 13, 14, 15, 16 is not mounted, the respective bristle holder 11, 12, 13, 14, 15, 16 is provided with a recess 23, 24. This recess 23, 24 is configured such that the respective mounting pin 8, 9 is prevented from making contact with the bristle holder 11, 12, 13, 14, 15, 16. This becomes apparent, for example, from FIG. 4 in which the bristle holder 16 includes a recess 24 configured such that the mounting pin 8 is not in a position to make contact with the bristle holder 16.

When the camshaft 4 is caused to rotate by means of the electric motor accommodated in the handle unit of the electric toothbrush, the cams 5 of the camshaft 4 act on the bristle holders 11, 12, 13, 14, 15, 16, imparting a motion to the bristle holders 11, 12, 13, 14, 15, 16 which will be described in greater detail in the following. On account of the identical configuration of the bristle holders 11, 12, 13, 14, 15, 16, this motion is identical for all bristle holders 11, 12, 13, 14, 15, 16. As a result of the 180-degree offset arrangement of the cams 5 on the camshaft 4, this motion is about 180 degrees out of phase for one pair of adjacent bristle holders 11, 12, 13, 14, 15, 16 each. Because of the alternate mounting of the bristle holders 11, 12, 13, 14, 15, 16 on the mounting pins 8, 9, this motion occurs in opposite directions for one pair of adjacent bristle holders 11, 12, 13, 14, 15, 16 each, as will be explained in the following.

The motion of the bristle holders 11, 12, 13, 14, 15, 16 produced by the cams 5 of the camshaft 4 will be explained in the following with reference to the bristle holder 13 illustrated in FIG. 3. In FIG. 3, reference numeral 25 is assigned to the tips of the bristle tuft 17 lying closest to the mounting pin 8, whereas the tips of the bristle tuft 17 lying farthest from the mounting pin 8 are designated by reference numeral 26. It will be understood that the subsequent description applies equally to the motion of the correspondingly driven bristle holders 11, 15.

In FIG. 3, the rotary motion of the camshaft 4 is indicated by an arrow. With the camshaft 4 performing such a rotary motion, it is because of the nearby mounting of the bristle holder 13 on the mounting pin 8 that the tips 25 will perform a reciprocating motion substantially transversely relative to the bristle tufts 17. When a user positions the bristle tufts 17 against the tooth surface at approximately right angles, such reciprocation amounts to a substantially wiping motion of the bristle tufts 17 approximately parallel to the tooth surface.

By contrast, the tips 26 will move on the arc of a circle having its center in the center of the mounting pin 8. In FIG. 3, this motion is designated by reference numeral 27. The motion 27 may be broken up into two components 28, 29 of motion at right angles to each other. When a user engages the bristle tufts against the tooth surface at approximately right angles, the component 29 moving approximately parallel to the bristle tufts 17 represents a pushing motion of the bristle tufts 17 approximately perpendicularly to the tooth surface. The component 28 moving transversely to the bristle tufts 17 represents a wiping motion of the bristle tufts 17 on the tooth surface.

The tips of the other bristle tufts 17 of the bristle holder 13 will perform motions whose components are between those of the tips 25 and the tips 26 of the two endmost bristle tufts 17. The tips of the bristle tufts 17 move on the arcs of circles having their center in the center of the mounting pin 8.

FIG. 4 shows the bristle holder 16 mounted on the mounting pin 9 by means of its opening 20 and moved by a cam 5 of the camshaft 4, which cam is spaced 180 degrees from the cam in the bristle holder 13 of FIG. 3. When the camshaft 4 is rotated, the tips of the bristle tufts 17 designated by reference numeral 30 and lying the farthest from the mounting pin 9 will move on the arc of a circle whose center is in the center of the mounting pin 9. In FIG. 4, this motion is assigned reference numeral 31. This motion 31 may be broken up into two components 32, 33 of motion at right angles to each other. The component 32 acts on the tooth surface in a pushing manner. The component 33 acts to wipe over the tooth surface. It will be understood that the foregoing description applies equally to the motion of the correspondingly driven bristle holders 12, 14.

In a modification of the embodiment described, the camshaft 4, rather than being caused to perform a continuous rotation, is caused to rotate in an oscillating fashion. In this modification, too, the bristle holders 11, 13, 15 and the bristle holders 12, 14, 16 alternately provide a pushing component moving in the direction of the tooth surface.

What is claimed is:

1. A brush unit for an electric toothbrush, said brush unit comprising:

a housing;

a camshaft rotatably mounted in said housing;

a first mounting pin extending approximately parallel to the camshaft;

a series of bristle holders disposed approximately transversely relative to and in contact with the camshaft, a first group of said series of bristle holders being pivotally mounted on said first mounting pin and being movable in a motion about the first mounting pin by rotation of the camshaft; and tufts of bristles mounted on said series of bristle holders, wherein said first mounting pin is disposed outside an imaginary first plane aligned approximately parallel to the bristle tufts and extending lengthwise through the camshaft.

2. A brush unit as claimed in claim 1, further comprising a second mounting pin which extends approximately parallel to the camshaft, wherein said first mentioned mounting pin and said second mounting pin are located on opposite sides of the imaginary first plane and wherein a second group of said series of bristle holders being pivotally mounted on said second mounting pin and being movable in a motion about the second mounting pin by the camshaft.

3. A brush unit as claimed in claim 2 wherein each of said bristle holders includes an opening receiving a corresponding one of said first and second mounting pins.

4. A brush unit as claimed in claim 3 wherein said first and second mounting pins are arranged in an imaginary second plane aligned approximately transversely relative to the bristle tufts and extending approximately parallel to the camshaft.

5. A brush unit as claimed in claim 3 wherein said first and second mounting pins are approximately parallel to each other, and the distances of said first and second mounting pins to the imaginary first plane are approximately equal.

6. A brush unit as claimed in claim 3, wherein each of the bristle holders has a recess in the area of the mounting pin on which it is not mounted, said recess being configured such as to enable the bristle holder to perform the motion produced by the camshaft without making contact with said mounting pin on which the bristle holder is not mounted.

7. A brush unit as claimed in claim 3, wherein each of the bristle holders includes an elongate hole for receiving the camshaft with the longitudinal axis of the elongate hole intersecting approximately the geometric axis of the associated mounting pin.

8. A brush unit as claimed in claims 6 or 7, wherein the bristle holders are of identical configuration, irrespective of their mounting on one of the two mounting pins.

9. A brush unit as claimed in claim 3, wherein the camshaft is adapted to perform an oscillating rotary motion.

10. A brush unit as claimed in claim 3, wherein the bristle holders are provided with different tufts of bristles.

\* \* \* \* \*